United States Patent
Nicholas et al.

(10) Patent No.: US 8,748,681 B2
(45) Date of Patent: *Jun. 10, 2014

(54) PROCESS FOR OLIGOMERIZING DILUTE ETHYLENE

(75) Inventors: Christopher P. Nicholas, Evanston, IL (US); Alakananda Bhattacharyya, Glen Ellyn, IL (US); David E. Mackowiak, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 615 days.

This patent is subject to a terminal disclaimer.

(21) Appl. No.: 12/416,026

(22) Filed: Mar. 31, 2009

(65) Prior Publication Data

US 2010/0249480 A1  Sep. 30, 2010

(51) Int. Cl.
*C07C 2/12* (2006.01)

(52) U.S. Cl.
USPC ........... 585/324; 585/326; 585/330; 585/648; 585/650; 585/653; 585/502; 585/512

(58) Field of Classification Search
USPC ......... 585/324, 326, 330, 648, 650, 651, 653, 585/502, 511, 512, 518, 519, 520, 531, 532, 585/533
See application file for complete search history.

(56) References Cited

U.S. PATENT DOCUMENTS

| | | | |
|---|---|---|---|
| 3,965,205 A | 6/1976 | Garwood et al. | |
| 4,028,227 A | 6/1977 | Gustafson | |
| 4,090,949 A | 5/1978 | Owen et al. | |
| 4,538,012 A | 8/1985 | Miller | |
| 4,551,438 A | 11/1985 | Miller | |
| 4,717,782 A | 1/1988 | Garwood et al. | |
| 4,822,477 A | 4/1989 | Avidan et al. | |
| 4,831,203 A | 5/1989 | Owen et al. | |
| 4,835,331 A * | 5/1989 | Hammershaimb et al. | ... 585/520 |
| 4,855,524 A | 8/1989 | Harandi et al. | |
| 4,855,528 A | 8/1989 | Young et al. | |
| 4,859,308 A | 8/1989 | Harandi et al. | |
| 4,861,934 A | 8/1989 | Suzuki et al. | |
| 4,935,568 A | 6/1990 | Harandi et al. | |
| 5,034,565 A | 7/1991 | Harandi et al. | |
| 5,205,924 A | 4/1993 | Betts et al. | |
| 5,324,417 A | 6/1994 | Harandi | |
| 5,702,589 A | 12/1997 | Tsang et al. | |
| 5,723,713 A | 3/1998 | Maunders | |
| 6,538,169 B1 * | 3/2003 | Pittman et al. | ................ 585/653 |
| 6,660,894 B1 | 12/2003 | Wu et al. | |
| 7,598,197 B2 | 10/2009 | Lattner et al. | |
| 2003/0045761 A1 * | 3/2003 | Kuechler et al. | ............. 585/327 |

(Continued)

OTHER PUBLICATIONS

Scurrell, M.S. et al., Oligomerization of ethene in a slurry reactor (II)-exchanged silica alumina catalyst, Journal of Catalysis 197(1) 2001 p. 49-57.

(Continued)

*Primary Examiner* — In Suk Bullock
*Assistant Examiner* — Sharon Pregler
(74) *Attorney, Agent, or Firm* — James C Paschall (57) ABSTRACT

The process and apparatus converts ethylene in a dilute ethylene stream that may be derived from an FCC product to heavier hydrocarbons. The catalyst may be an amorphous silica-alumina base with a Group VIII and/or VIB metal. The catalyst is resistant to feed impurities such as hydrogen sulfide, carbon oxides, hydrogen and ammonia. At least 40 wt-% of the ethylene in the dilute ethylene stream can be converted to heavier hydrocarbons.

17 Claims, 4 Drawing Sheets

(56) References Cited

U.S. PATENT DOCUMENTS

| | | |
|---|---|---|
| 2003/0094398 A1 | 5/2003 | Porter et al. |
| 2005/0038306 A1 | 2/2005 | Beech et al. |
| 2006/0063955 A1* | 3/2006 | Lacombe et al. ............ 585/535 |
| 2006/0135836 A1 | 6/2006 | Beech, Jr. et al. |
| 2006/0149111 A1 | 7/2006 | Van Egmond et al. |
| 2006/0194995 A1 | 8/2006 | Umansky et al. |

OTHER PUBLICATIONS

Heveling, J. et al., "Activity and selectivity of nickel-exchanged silica-alumina catalysts . . . ", Applied Catalysis A: General 248 (1/2) 2003 p. 237-248.

Tkach V.S. et al., "Dimerization of propylene and oligomerization of ethylene over supported nickel catalysts". Inst. of Organic Chem. Russian Academy of Sciences.

Hulea, V. et al., "Ni-exchanged AlMCM-41—An Efficient bifunctional catalyst for ethylene oligomerization", Journal of Catalysis 225(1) 2004 p. 213-222.

Lallemand, M. et al., "Catalytic oligomerization of ethylene over Ni-containing dealuminated Y zeolites", Applied catalysis A: General 201(2) 2006 p. 196-201 Elsevier.

Heveling, J. et al., "Catalysts and conditions for highly efficient and stable heterogeneous oligomerization of ethylene", ACS 202nd National Meeting, V36 N.4 578-84 (Aug. 1991).

Nesterov, G.A. et al., "Supported nickel catalysts for ethylene oligomerization", Journal of Molecular Catalysis V69 N.1 129-36 (Oct. 1, 1991) Elsevier.

Hartmann, M. et al., "Ethylene dimerization in nickel containing MCM-41 and AlMCM-41 . . . ", Studies in Surface Science and Catalysis V101B 801-9 (1996).

Diaz, G.C. et al., "Production of (oligomeric) olefins with (3,4,5,7, or 9 (percent) nickel/zeolite catalysts", 175th SGC Natl Meet (Anaheim, CA, Mar. 12, 1978, Pet Chem Prepr.

Al-Jarallah A.M. et al., "Ethylene dimerication and oligomerization to butene-1 and linear (ALPHA)-olefins", Catalysis Today, V14 N.1 1-124 (Apr. 10, 1992) Elsevier.

Heveling J. et al., "Oligomerization of ethene over nickel-exchanged zeolite y into a diesel-range product", Appl. Catal. V42, N.2 325-36 (Sep. 15, 1988) Elsevier.

\* cited by examiner

PROCESS FOR OLIGOMERIZING DILUTE ETHYLENE

BACKGROUND OF THE INVENTION

The field of the invention is an apparatus and process for converting diluted ethylene in a hydrocarbon stream to heavier hydrocarbons. These heavier hydrocarbons may be used as motor fuels.

Dry gas is the common name for the off-gas stream from a fluid catalytic cracking unit that contains all the gases with boiling points lower than ethane. The off-gas stream is compressed to remove as much of the $C_3$ and $C_4$ gases as possible. Sulfur is also largely absorbed from the off-gas stream in a scrubber that utilizes an amine absorbent. The remaining stream is known as the FCC dry gas. A typical dry gas stream contains 5 to 50 wt-% ethylene, 10 to 20 wt-% ethane, 5 to 20 wt-% hydrogen, 5 to 20 wt-% nitrogen, about 0.1 to about 5.0 wt-% of each carbon monoxide and carbon dioxide and less than 0.01 wt-% hydrogen sulfide and ammonia with the balance being methane.

Currently, the FCC dry gas stream is sent to a burner as fuel gas. An FCC unit that processes 7,949 kiloliters (50,000 barrels) per day will burn about 181,000 kg (200 tons) of dry gas with about 36,000 kg (40 tons) of ethylene as fuel per day. Because a large price difference exists between fuel gas and motor fuel products or pure ethylene it would appear economically advantageous to attempt to recover this ethylene. However, the dry gas stream contains impurities that can poison oligomerization catalyst and is so dilute that ethylene recovery is not economically justified by gas recovery systems.

The oligomerization of concentrated ethylene streams to liquid products is a known technology. However, oligomerization typically involves the use of propylene or butylene particularly from liquefied petroleum gas (LPG) or dehydrogenated feedstocks to make gasoline range olefins. Ethylene is little used as an oligomerization feedstock because of its much lower reactivity.

There is need for utilization of dilute ethylene in refinery streams.

SUMMARY OF THE INVENTION

We have found that ethylene in dilute ethylene streams, such as an FCC dry gas stream, can be catalytically oligomerized to heavier hydrocarbons with a Group VIII and/or Group VIB metal on amorphous silica-alumina catalyst. The heavier hydrocarbons can be separated and blended in the gasoline and diesel pools. We have found zeolitic catalysts that are suitable for oligomerization of ethylene quickly deactivate in the presence of impurities such as carbon oxides, ammonia and hydrogen sulfide. The impurities do not substantially affect a catalyst comprising a Group VIII and/or VIB metal on amorphous silica-alumina support. Consequently, dilute ethylene in an FCC dry gas stream can be oligomerized to a liquid fuel product which is easy to separate from the unconverted gas stream. The unconverted gas can then be burned as fuel gas, but with the more valuable ethylene removed as heavier hydrocarbons.

Advantageously, the process and apparatus can enable utilization of ethylene in a dilute stream and in the presence of feed impurities that can be catalyst poisons.

Additional features and advantages of the invention will be apparent from the description of the invention, the FIGURES and claims provided herein.

DETAILED DESCRIPTION

The present invention may be applied to any hydrocarbon stream containing ethylene and, preferably, a dilute proportion of ethylene. A suitable, dilute ethylene stream may typically comprise between about 5 and about 50 wt-% ethylene. An FCC dry gas stream is a suitable dilute ethylene stream. Other dilute ethylene streams may also be utilized in the present invention such as coker dry gas streams. Because the present invention is particularly suited to FCC dry gas, the subject application will be described with respect to utilizing ethylene from an FCC dry gas stream.

Figure 1:
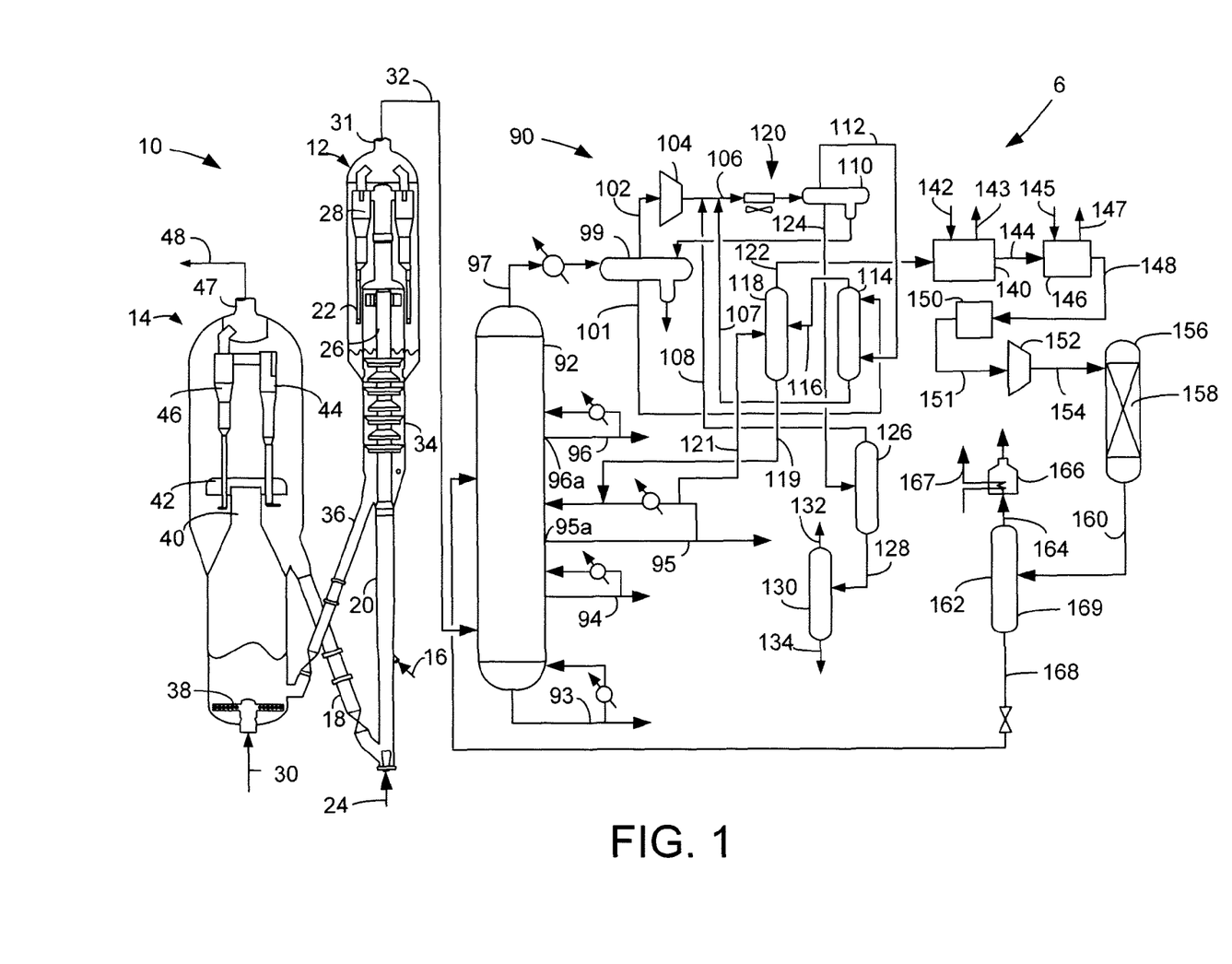
FIG. 1 is a schematic drawing of an FCC unit and an FCC product recovery system.

Now turning to FIG. 1, wherein like numerals designate like components, FIG. 1 illustrates a refinery complex 6 that generally includes an FCC unit section 10 and a product recovery section 90. The FCC unit section 10 includes a reactor 12 and a catalyst regenerator 14. Process variables typically include a cracking reaction temperature of 400° to 600° C. and a catalyst regeneration temperature of 500° to 900° C. Both the cracking and regeneration occur at an absolute pressure below 506 kPa (72.5 psia).

FIG. 1 shows a typical FCC reactor 12 in which a heavy hydrocarbon feed or raw oil stream in a distributor 16 is contacted with a regenerated cracking catalyst entering from a regenerated catalyst standpipe 18. This contacting may occur in a narrow riser 20, extending upwardly to the bottom of a reactor vessel 22. The contacting of feed and catalyst is fluidized by gas from a fluidizing line 24. In an embodiment, heat from the catalyst vaporizes the hydrocarbon feed or oil, and the hydrocarbon feed is thereafter cracked to lighter molecular weight hydrocarbon products in the presence of the catalyst as both are transferred up the riser 20 into the reactor vessel 22. Inevitable side reactions occur in the riser 20 leaving coke deposits on the catalyst that lower catalyst activity. The cracked light hydrocarbon products are thereafter separated from the coked cracking catalyst using cyclonic separators which may include a primary separator 26 and one or two stages of cyclones 28 in the reactor vessel 22. Gaseous, cracked products exit the reactor vessel 22 through a product outlet 31 to line 32 for transport to a downstream product recovery section 90. The spent or coked catalyst requires regeneration for further use. Coked cracking catalyst, after separation from the gaseous product hydrocarbons, falls into a stripping section 34 where steam is injected through a nozzle to purge any residual hydrocarbon vapor. After the stripping operation, the coked catalyst is carried to the catalyst regenerator 14 through a spent catalyst standpipe 36.

FIG. 1 depicts a regenerator 14 known as a combustor. However, other types of regenerators are suitable. In the catalyst regenerator 14, a stream of oxygen-containing gas, such as air, is introduced through an air distributor 38 to contact the coked catalyst. Coke is combusted from the coked catalyst to provide regenerated catalyst and flue gas. The catalyst regeneration process adds a substantial amount of heat to the catalyst, providing energy to offset the endothermic cracking reactions occurring in the reactor riser 20. Catalyst and air flow upwardly together along a combustor riser 40 located within the catalyst regenerator 14 and, after regeneration, are initially separated by discharge through a disengager 42. Additional recovery of the regenerated catalyst and flue gas exiting the disengager 42 is achieved using first and second stage separator cyclones 44, 46, respectively within the catalyst regenerator 14. Catalyst separated from flue gas dispenses through diplegs from cyclones 44, 46 while flue gas relatively lighter in catalyst sequentially exits cyclones 44, 46 and exits the regenerator vessel 14 through flue gas outlet 47 in flue gas line 48. Regenerated catalyst is carried back to the riser 20 through the regenerated catalyst standpipe 18. As a result of the coke burning, the flue gas vapors exiting at the top of the catalyst regenerator 14 in line 48 contain CO, $CO_2$, $N_2$ and $H_2O$, along with smaller amounts of other species. Hot flue gas exits the regenerator 14 through the flue gas outlet 47 in a line 48 for further processing.

The product recovery section 90 is in downstream communication with the product outlet 31. "Downstream communication" means that at least a portion of material flowing to the component in downstream communication may operatively flow from the component with which it communicates. "Communication" means that material flow is operatively permitted between enumerated components. In the product recovery section 90, the gaseous FCC product in line 32 is directed to a lower section of an FCC main fractionation column 92. The main column 92 is in downstream communication with the product outlet 31. Several fractions of FCC product may be separated and taken from the main column including a heavy slurry oil from the bottoms in line 93, a heavy cycle oil stream in line 94, a light cycle oil in line 95 taken from outlet 95a and a heavy naphtha stream in line 96 taken from outlet 96a. Any or all of lines 93-96 may be cooled and pumped back to the main column 92 to cool the main column typically at a higher location. Gasoline and gaseous light hydrocarbons are removed in overhead line 97 from the main column 92 and condensed before entering a main column receiver 99. The main column receiver 99 is in downstream communication with the product outlet 31, and the main column 92 is in upstream communication with the main column receiver 99. "Upstream communication" means that at least a portion of the material flowing from the component in upstream communication may operatively flow to the component with which it communicates.

An aqueous stream is removed from a boot in the receiver 99. Moreover, a condensed light naphtha stream is removed in line 101 while an overhead stream is removed in line 102. The overhead stream in line 102 contains gaseous light hydrocarbon which may comprise a dilute ethylene stream. The streams in lines 101 and 102 may enter a vapor recovery section 120 of the product recovery section 90.

The vapor recovery section 120 is shown to be an absorption based system, but any vapor recovery system may be used including a cold box system. To obtain sufficient separation of light gas components the gaseous stream in line 102 is compressed in compressor 104. More than one compressor stage may be used, but typically a dual stage compression is utilized. The compressed light hydrocarbon stream in line 106 is joined by streams in lines 107 and 108, chilled and delivered to a high pressure receiver 110. An aqueous stream from the receiver 110 may be routed to the main column receiver 99. A gaseous hydrocarbon stream in line 112 comprising the dilute ethylene stream is routed to a primary absorber 114 in which it is contacted with unstabilized gasoline from the main column receiver 99 in line 101 to effect a separation between $C_3+$ and $C_2-$ hydrocarbons. The primary absorber 114 is in downstream communication with the main column receiver 99. A liquid $C_3+$ stream in line 107 is returned to line 106 prior to chilling. A primary off-gas stream in line 116 from the primary absorber 114 comprises the dilute ethylene stream for purposes of the present invention. However, to concentrate the ethylene stream further and to recover heavier components line 116 may optionally be directed to a secondary absorber 118, where a circulating stream of light cycle oil in line 121 diverted from line 95 absorbs most of the remaining $C_5+$ and some $C_3$-$C_4$ material in the primary off-gas stream. The secondary absorber 118 is in downstream communication with the primary absorber 114. Light cycle oil from the bottom of the secondary absorber in line 119 richer in $C_3+$ material is returned to the main column 92 via the pump-around for line 95. The overhead of the secondary absorber 118 comprising dry gas of predominantly $C_2-$ hydrocarbons with hydrogen sulfide, ammonia, carbon oxides and hydrogen is removed in a secondary off-gas stream in line 122 to comprise a dilute ethylene stream.

Liquid from the high pressure receiver 110 in line 124 is sent to a stripper 126. Most of the $C_2-$ is removed in the overhead of the stripper 126 and returned to line 106 via overhead line 108. A liquid bottoms stream from the stripper 126 is sent to a debutanizer column 130 via line 128. An overhead stream in line 132 from the debutanizer comprises $C_3$-$C_4$ olefinic product while a bottoms stream in line 134 comprising stabilized gasoline may be further treated and sent to gasoline storage.

The dilute ethylene stream of the present invention may comprise an FCC dry gas stream comprising between about 5 and about 50 wt-% ethylene and preferably about 10 to about 30 wt-% ethylene. Methane will typically be the predominant component in the dilute ethylene stream at a concentration of between about 25 and about 55 wt-% with ethane being substantially present at typically between about 5 and about 45 wt-%. Between about 1 and about 25 wt-% and typically about 5 to about 20 wt-% of hydrogen and nitrogen each may be present in the dilute ethylene stream. Saturation levels of water may also be present in the dilute ethylene stream. If secondary absorber 118 is used, no more than about 5 wt-% of $C_3+$ will be present with typically less than 0.5 wt-% propylene.

Besides hydrogen, other impurities such as hydrogen sulfide, ammonia, carbon oxides and acetylene may also be present in the dilute ethylene stream.

We have found that many impurities in a dry gas ethylene stream can poison an oligomerization catalyst. Hydrogen and carbon monoxide can reduce the metal sites to inactivity. Carbon dioxide and ammonia can attack acid sites on the catalyst. Hydrogen sulfide can attack metals on a catalyst to produce metal sulfides. Acetylene can polymerize and gum up on the catalyst or equipment.

The secondary off-gas stream in line 122, comprising a dilute ethylene stream may be introduced into an optional amine absorber unit 140 to remove hydrogen sulfide to lower concentrations. A lean aqueous amine solution, such as comprising monoethanol amine or diethanol amine, is introduced via line 142 into absorber 140 and is contacted with the flowing secondary off-gas stream to absorb hydrogen sulfide, and a rich aqueous amine absorption solution containing hydrogen sulfide is removed from absorption zone 140 via line 143 and recovered and perhaps further processed.

The amine-treated dilute ethylene stream in line 144 may be introduced into an optional water wash unit 146 to remove residual amine carried over from the amine absorber 140 and reduce the concentration of ammonia and carbon dioxide in the dilute ethylene stream in line 144. Water is introduced to the water wash in line 145. The water in line 145 is typically slightly acidified to enhance capture of basic molecules such as the amine. An aqueous stream in line 147 rich in amine and potentially ammonia and carbon dioxide leaves the water wash unit 146 and may be further processed.

The optionally amine treated dilute ethylene and perhaps water washed stream in line 148 may then be treated in an optional guard bed 150 to remove one or more of the impurities such as carbon monoxide, hydrogen sulfide and ammonia down to lower concentrations. The guard bed 150 may contain an adsorbent to adsorb impurities such as hydrogen sulfide that may poison an oligomerization catalyst. The guard bed 150 may contain multiple adsorbents for adsorbing more than one type of impurity. A typical adsorbent for adsorbing hydrogen sulfide is ADS-12, for adsorbing CO is ADS-106 and for adsorbing ammonia is UOP MOLSIV 3A all available from UOP, LLC. The adsorbents may be mixed in a single bed or can be arranged in successive beds.

A dilute ethylene stream in line 151 perhaps amine treated, perhaps water washed and perhaps adsorption treated to remove more hydrogen sulfide, ammonia and carbon monoxide will typically have at least one of the following impurity concentrations: about 0.1 wt-% and up to about 5.0 wt-% of carbon monoxide and/or about 0.1 wt-% and up to about 5.0 wt-% of carbon dioxide, and/or at least about 1 wppm and up to about 500 wppm hydrogen sulfide and/or at least about 1 and up to about 500 wppm ammonia, and/or at least about 5 and up to about 20 wt-% hydrogen. The type of impurities present and their concentrations will vary depending on the processing and origin of the dilute ethylene stream.

Line 151 carries the dilute ethylene stream to a compressor 152 to be pressured up to reactor pressure. The compressor 152 is in downstream communication with the main column 92, the product recovery section 90 and the product outlet 31. The compressed dilute ethylene stream can be compressed to at least about 3,550 kPa (500 psia) and perhaps no more than about 10,445 kPa (1500 psia) and suitably between about 4,930 kPa (700 psia) and about 7,687 kPa (1100 psia). It is preferred that the dilute ethylene stream be pressured up to above the critical pressure of ethylene which is about 4,992 kPa (724 psia) for pure ethylene to avoid rapid catalyst deactivation. The compressor 152 may comprise one or more stages with interstage cooling. A heater may be required to bring the compressed stream up to reaction temperature. The compressed dilute ethylene is carried in line 154 to oligomerization reactor 156.

The oligomerization reactor 156 is in downstream communication with the compressor 152 and the primary and secondary absorbers 114 and 118, respectively. The oligomerization reactor preferably contains a fixed catalyst bed 158. The dilute ethylene feed stream contacts the catalyst preferably in a down flow operation. However, upflow operation may be suitable. The catalyst is preferably an amorphous silica-alumina base with a metal from either Group VIII and/or Group VIB in the periodic table using Chemical Abstracts Service notations. In an aspect, the catalyst has a Group VIII metal promoted with a Group VIB metal. In an aspect, the catalyst has a silica-to-alumina ratio of no more than 30 and preferably no more than 20. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Catalysts for the present invention may have a Low Temperature Acidity Ratio of at least about 0.15, suitably of about 0.2, and preferably greater than about 0.25, as determined by Ammonia Temperature Programmed Desorption (Ammonia TPD) as described hereinafter. Additionally, a suitable catalyst will have a surface area of between about 50 and about 400 $m^2/g$ as determined by nitrogen BET.

A preferred oligomerization catalyst of the present invention is described as follows. The preferred oligomerization catalyst comprises an amorphous silica-alumina support. One of the components of the catalyst support utilized in the present invention is alumina. The alumina may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A particularly preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina. Another component of the catalyst support is an amorphous silica-alumina. A suitable silica-alumina with a silica-to-alumina ratio of 2.6 is available from CCIC, a subsidiary of JGC, Japan.

Another component utilized in the preparation of the catalyst utilized in the present invention is a surfactant. The surfactant is preferably admixed with the hereinabove described alumina and the silica-alumina powders. The resulting admixture of surfactant, alumina and silica-alumina is then formed, dried and calcined as hereinafter described. The calcination effectively removes by combustion the organic components of the surfactant but only after the surfactant has dutifully performed its function in accordance with the present invention. Any suitable surfactant may be utilized in accordance with the present invention. A preferred surfactant is a surfactant selected from a series of commercial surfactants sold under the trademark "Antarox" by Solvay S.A. The "Antarox" surfactants are generally characterized as modified linear aliphatic polyethers and are low-foaming biodegradable detergents and wetting agents.

A suitable silica-alumina mixture is prepared by mixing proportionate volumes silica-alumina and alumina to achieve the desired silica-to-alumina ratio. In an embodiment, 85 wt-% amorphous silica-alumina with a silica-to-alumina ratio of 2.6 and 15 wt-% alumina powder will provide a suitable support. In an embodiment, ratios other than 85-to-15 of amorphous silica-alumina to alumina may be suitable, so long as the final silica-to-alumina ratio of the support is suitably no more than 30 and preferably no more than 20.

Any convenient method may be used to incorporate a surfactant with the silica-alumina and alumina mixture. The surfactant is preferably admixed during the admixture and formation of the alumina and silica-alumina. A preferred method is to admix an aqueous solution of the surfactant with the blend of alumina and silica-alumina before the final formation of the support. It is preferred that the surfactant be present in the paste or dough in an amount from about 0.01 to about 10 wt-% based on the weight of the alumina and silica-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough mixture of alumina, silica-alumina, surfactant and water through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch). Among the preferred catalyst configurations are cross-sectional shapes resembling that of a three-leaf clover, as shown, for example, in FIGS. 8 and 8A of U.S. Pat. No. 4,028,227. Preferred clover-shaped particulates are such that each "leaf" of the cross-section is defined by about a 270° arc of a circle having a diameter between about 0.51 mm (0.02 inch) and 1.27 mm (0.05 inch). Other preferred particulates are those having quadralobal cross-sectional shapes, including asymmetrical shapes, and symmetrical shapes such as in FIG. 10 of U.S. Pat. No. 4,028,227.

Typical characteristics of the amorphous silica-alumina supports utilized herein are a total pore volume, average pore diameter and surface area large enough to provide substantial space and area to deposit the active metal components. The total pore volume of the support, as measured by conventional mercury porosimeter methods, is usually about 0.2 to about 2.0 cc/gram, preferably about 0.25 to about 1.0 cc/gram and most preferably about 0.3 to about 0.9 cc/gram. Ordinarily, the amount of pore volume of the support in pores of diameter greater than 100 angstroms is less than about 0.1 cc/gram, preferably less than 0.08 cc/gram, and most preferably less than about 0.05 cc/gram. Surface area, as measured by the B.E.T. method, is typically above 50 m$^2$/gram, e.g., above about 200 m$^2$/gram, preferably at least 250 m$^2$/gram., and most preferably about 300 m$^2$/gram to about 400 m$^2$/gram.

To prepare the catalyst, the support material is compounded, as by a single impregnation or multiple impregnations of a calcined amorphous refractory oxide support particles, with one or more precursors of at least one metal component from Group VIII or VIB of the periodic table. The Group VIII metal, preferably nickel, should be present in a concentration of about 0.5 to about 15 wt-% and the Group VIB metal, preferably tungsten, should be present in a concentration of about 0 to about 12 wt-%. The impregnation may be accomplished by any method known in the art, as for example, by spray impregnation wherein a solution containing the metal precursors in dissolved form is sprayed onto the support particles. Another method is the multi-dip procedure wherein the support material is repeatedly contacted with the impregnating solution with or without intermittent drying. Yet other methods involve soaking the support in a large volume of the impregnation solution or circulating the support therein, and yet one more method is the pore volume or pore saturation technique wherein support particles are introduced into an impregnation solution of volume just sufficient to fill the pores of the support. On occasion, the pore saturation technique may be modified so as to utilize an impregnation solution having a volume between 10 percent less and 10 percent more than that which will just fill the pores.

If the active metal precursors are incorporated by impregnation, a subsequent or second calcination at elevated temperatures, as for example, between 399° and 760° C. (750° and 1400° F.), converts the metals to their respective oxide forms. In some cases, calcinations may follow each impregnation of individual active metals. A subsequent calcination yields a catalyst containing the active metals in their respective oxide forms.

A preferred oligomerization catalyst of the present invention has an amorphous silica-alumina base impregnated with 0.5-15 wt-% nickel in the form of 3.175 mm (0.125 inch) extrudates and a density of about 0.45 to about 0.65 g/ml. It is also contemplated that metals can be incorporated onto the support by other methods such as ion-exchange and co-mulling.

An alternative catalyst suitable for the present invention utilizes a co-gelled silica-alumina support made by the well-known oil-drop method which permits the utilization of the support in the form of macrospheres. For example, an alumina sol, utilized as an alumina source, is commingled with an acidified water glass solution as a silica source, and the mixture is further commingled with a suitable gelling agent, for example, urea, hexamethylenetetramine, or mixtures thereof. The mixture is discharged while still below gellation temperature, and by means of a nozzle or rotating disk, into a hot oil bath maintained at gellation temperature. The mixture is dispersed into the oil bath as droplets which form into spheroidal gel particles during passage therethrough. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period of at least 10 to 16 hours, and then in a suitable alkaline or basic medium for at least 3 to about 10 hours, and finally water-washed. Proper gellation of the mixture in the oil bath, as well as subsequent aging of the gel spheres, is not readily accomplished below about 48.9° C. (120° F.), and at about 98.9° C. (210° F.), the rapid evolution of the gases tend to rupture and otherwise weaken the spheres. By maintaining sufficient superatmospheric pressure during the forming and aging steps in order to maintain water in the liquid phase, a higher temperature can be employed, frequently with improved results. If the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature of from about 93.3° C. (200° F.) to about 315° C. (600° F.) for a period of from about 6 to about 24 hours or more, and then calcined at a temperature of from about 426.67° C. (800° F.) to about 760° C. (1400° F.) for a period of from 2 to about 12 hours or more.

The Group VIII component and the Group VIB component are composed with the co-gelled silica-alumina carrier material by any suitable co-impregnation technique. Thus, the carrier material can be soaked, dipped, suspended, or otherwise immersed in an aqueous impregnating solution containing a soluble Group VIII salt and a soluble Group VIB salt. One suitable method comprises immersing the carrier material in the impregnating solution and evaporating the same to dryness in a rotary steam dryer, the concentration of the impregnating solution being such as to ensure a final catalyst composite comprising an atomic ratio of nickel to nickel plus tungsten of about 0.1 to about 0.3. Another suitable method comprises dipping the carrier material into the aqueous impregnating solution at room temperature until complete penetration of carrier by the solution is achieved. After absorption of the impregnating solution, the carrier is drained of free surface liquid and dried in a moving belt calciner.

The catalyst composite is usually dried at a temperature of from about 93.3° C. (200° F.) to about 260° C. (500° F.) for a period of from about 1 to about 10 hours prior to calcination. In accordance with the present invention, calcination is effected in an oxidizing atmosphere at a temperature of from about 371° C. (700° F.) to about 650° C. (1200° F.). The oxidizing atmosphere is suitably air, although other gases comprising molecular oxygen may be employed.

A suitable alternative catalyst is an oil dropped silica-alumina spherical support with a diameter of 3.175 mm (0.125 inch) impregnated with about 0.5 to about 15 wt-% nickel and with 0 to about 12 wt-% tungsten. Other metals incorporation methods may be suitable and are contemplated. A suitable density range for the alternative catalyst would be between about 0.60 and about 0.70 g/mL.

The dilute ethylene feed may be contacted with the oligomerization catalyst at a temperature between about 200° and about 400° C. The reaction takes place predominantly in the gas phase at a GHSV 50 to 1000 $hr^{-1}$ on ethylene basis. We have found, surprisingly, that despite the presence of impurities in the feed that poison the catalyst and dilution of the ethylene in the feed, that at least about 40 wt-% and as much as about 75 wt-% of the ethylene in the feed stream convert to heavier hydrocarbons. The ethylene will first oligomerize over the catalyst to heavier olefins. Some of the heavier olefins may cyclize over the catalyst, and the presence of hydrogen could facilitate conversion of the olefins to paraffins which are all heavier hydrocarbons than ethylene.

The catalyst remains stable despite the impure feed, but it can be regenerated upon deactivation. Suitable regeneration conditions include subjecting the catalyst, for example, in situ, to hot air at 500° C. for 3 hours. Activity and selectivity of the regenerated catalyst is comparable to fresh catalyst.

The oligomerization product stream from the oligomerization reactor in line 160 can be transported to an oligomerization separator 162 which may be a simple flash drum to separate a gaseous stream from a liquid stream. The oligomerization separator 162 is in downstream communication with the oligomerization reactor 156. The gaseous product stream in overhead line 164 comprising light gases such as hydrogen, methane, ethane, unreacted olefins and light impurities may be transported to a combustion unit 166 to generate steam in line 167. Alternatively, the gaseous product in overhead line 164 may be combusted to fire a heater (not shown) and/or to provide a source of flue gas to turn a gas turbine (not shown) to generate power. The overhead line 164 is in upstream communication with the combustion unit 166. The liquid bottoms stream comprising heavier hydrocarbons in line 168 from the oligomerization separator 162 can be let down over a valve and recycled back to the product separation section 90. The recycle line 168 is in downstream communication with a bottoms 169 of the oligomerization separator 162. Consequently, the main column 92 is in downstream and upstream communication with the oligomerization reactor 156. The bottoms stream is preferably recycled via recycle line 168 to the main column 92 at a location between the heavy naphtha outlet 96a and the light cycle oil outlet 95a. Alternatively, the recycle line 168 feeds the light cycle oil line 95 or the heavy naphtha line 96. The recycle line is in downstream communication with the oligomerization reactor 156 and in upstream communication with the main column 92. Alternatively, the oligomerization product in lines 160 or 168 may be saturated or not and transported to a fuel tank without recycling to the product separation zone 90.

EXAMPLES

The utility of the present invention will be demonstrated by the following examples.

Example 1

A nickel and tungsten on an amorphous silica-alumina oil-dropped spherical base was synthesized via the procedures given hereinabove for the alternative catalyst of the present invention. The metals comprised 1.5 wt-% nickel and 11 wt-% tungsten of the catalyst. The spherical bases had diameters of 3.175 mm. The catalyst had a silica-to-alumina ratio of about 3, a density of 0.641 g/mL and a surface area of 371 $m^2/g$.

Example 2

An extruded amorphous silica-alumina was synthesized by combining an amorphous silica-alumina having a silica-to-alumina ratio of about 2.6 provided by CCIC, and pseudo-boehmite provided under the Catapal trademark in a weight ratio of 85-to-15. The pseudo-boehmite was peptized with nitric acid before mixture with the amorphous silica-alumina. A surfactant provided under the Antarox trademark and water in sufficient quantity to wet the dough were added to the mixture. The catalyst dough was extruded through 1.59 mm openings in a cylindrical die plate and broken into pieces prior to calcination at 550° C. The finished catalyst consisted of 85 wt-% silica-alumina and 15 wt-% alumina, had a silica-to-alumina ratio of 1.92 and had a surface area of 368 $m^2/g$.

Example 3

Of $Ni(NO_3)_2.6H_2O$, 3.37 grams was dissolved in 32.08 grams of deionized water. The nickel solution was contacted with the extruded amorphous silica-alumina of Example 2 by adding the nickel solution in fourths and shaking vigorously between additions. A light green extrudate resulted. The nickel metal was then converted to the oxide form by drying the extrudates at 110° C. for 3 hours, then calcining by ramping to 500° C. at 2° C./min and holding at 500° C. for 3 hours before cooling to room temperature. The light gray extrudates were found to contain 1.5 wt-% nickel.

Example 4

A sample of MTT zeolite with a silica-to-alumina ratio of 40 was obtained from the Zeolyst Corporation. The MTT zeolite was combined with pseudo-boehmite and extruded through 3.175 mm openings in a cylindrical die plate before calcining to 550° C. The finished catalyst consisted of 80 wt-% MTT zeolite and 20 wt-% alumina.

Example 5

The catalyst of Example 1 was tested for olefin oligomerization at 280° C., 6,895 kPa (1000 psig), 58 OGHSV (olefin gas hourly space velocity) in a fixed bed operation over 10 mL of catalyst. The feed consisted of 30 wt-% $C_2H_4$ and 70 wt-% $CH_4$. Results are shown in Table I.

Example 6

The catalyst of Example 2 was tested for olefin oligomerization at 280° C., 6,895 kPa (1000 psig), 586 OGHSV in a fixed bed operation over 10 mL of catalyst. The feed consisted of 23 wt-% $C_2H_4$, 14 wt-% $C_2H_6$, 35 wt-% $CH_4$, 13 wt-% $H_2$, 13 wt-% $N_2$, 1 wt-% CO, 1.5 wt-% $CO_2$, 10 wppm $H_2S$ and was saturated with water vapor at 25° C. and 3,447 kPa (500 psig) prior to feeding the oligomerization reaction. Results are shown in the Table I and in FIG. 2.

Example 7

The catalyst of Example 3 was tested for olefin oligomerization at 280° C., 6,895 kPa (1000 psig), 586 OGHSV in a fixed bed operation over 10 mL of catalyst. The feed consisted of 23 wt-% $C_2H_4$, 14 wt-% $C_2H_6$, 35 wt-% $CH_4$, 13 wt-% $H_2$, 13 wt-% $N_2$, 1 wt-% CO, 1.5 wt-% $CO_2$, 10 wppm $H_2S$ and was saturated with water vapor at 25° C. and 3,447 kPa (500 psig) prior to feeding the oligomerization reaction. Results are shown in Table I and FIG. 2. During 27-44 hours on stream, 1 ppm $NH_3$ was also added to the feed. No changes in conversion or selectivity were noted.

Example 8

The experiment of Example 7 was repeated except that the concentration of $H_2S$ in the feed was 50 wppm rather than 10 wppm. Results are shown in Table I and in FIG. 2.

Figure 2:
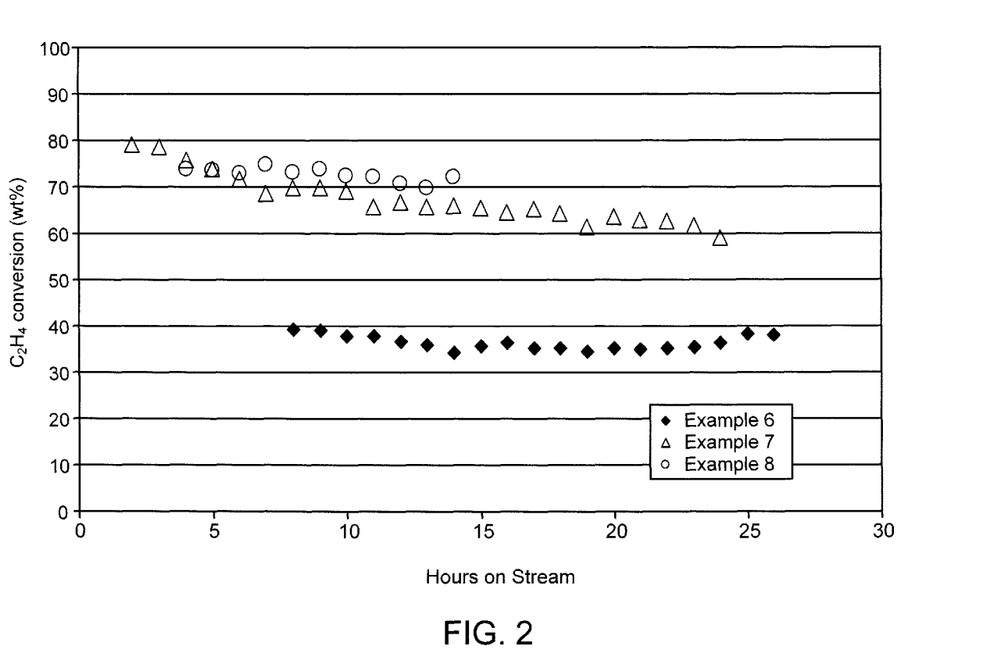
FIG. 2 is a plot of ethylene conversion versus time on stream for Examples 6-8.

FIG. 2 is a plot of $C_2H_4$ conversion versus time on stream for Examples 6-8. The nickel on amorphous silica-alumina catalyst of Example 3 performed better than just the silica-alumina base of Example 2 in terms of ethylene conversion. The catalysts of Examples 2 and 3 were also little affected by feed impurities.

Example 9

The catalyst of Example 4 was tested for olefin oligomerization at 280° C., 6,895 kPa (1000 psig), 586 OGHSV in a fixed bed operation over 10 mL of catalyst. The feed consisted of 23 wt-% $C_2H_4$, 14 wt-% $C_2H_6$, 35 wt-% $CH_4$, 13 wt-% $H_2$, 13 wt-% $N_2$, 1 wt-% CO, 1.5 wt-% $CO_2$, 10 wppm $H_2S$ and was saturated with water vapor at 25° C. and 3,447 kPa (500 psig) prior to feeding the oligomerization reaction. Results are shown in Table I and in FIG. 3.

Figure 3:
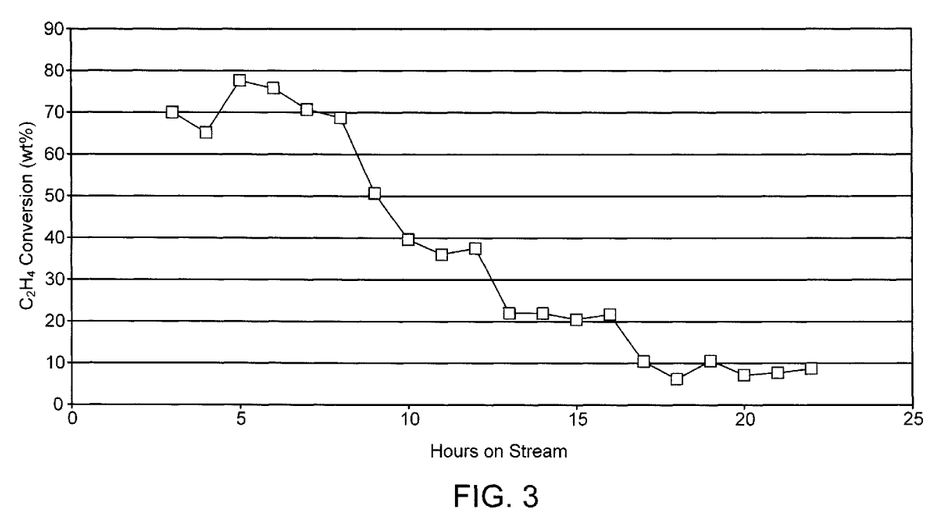
FIG. 3 is a plot of ethylene conversion versus time on stream for Example 9.

FIG. 3 is a plot of $C_2H_4$ conversion versus time on stream for Example 9 showing the effect of impurities that can poison the MTT zeolite catalyst of Example 4. After 20 hours of reaction, conversion had dropped to below 10 wt-%, while conversion by the catalyst from Example 3 in Examples 7 and 8 were maintained around 60 wt-%.

Example 10

The catalyst of example 4 was tested for olefin oligomerization at 280° C., 6,895 kPa (1000 psig) kPa, 613 OGHSV in a fixed bed operation over 10 mL catalyst. The feed consisted of 30 wt-% $C_2H_4$ and 70 wt-% $CH_4$. At 21 hours on stream, hydrogen was added to achieve a feed consisting of 27 wt-% $C_2H_4$, 63 wt-% $CH_4$ and 10 wt-% $H_2$. At 45 hours on stream, 500 wppm $NH_3$ in $H_2$ was added to achieve a feed of 27 wt-% $C_2H_4$, 63 wt-% $CH_4$, 10 wt-% $H_2$ and 50 wppm $NH_3$. Results are shown in Table I and in FIG. 4.

Figure 4:
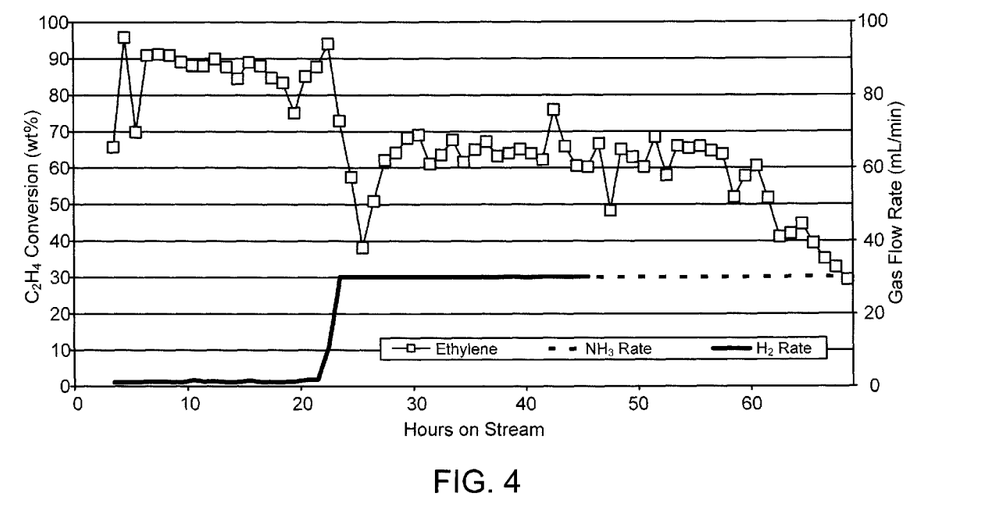
FIG. 4 is a plot of ethylene conversion versus time on stream from Example 10.

FIG. 4 is a plot of $C_2H_4$ conversion versus time on stream from Example 10 showing the effect of impurities $H_2$ and $NH_3$ on the MTT zeolite catalyst of Example 4. As can be seen in FIG. 3, ethylene conversion dropped upon introduction of hydrogen to the feed at 20 hours on stream. Additionally, upon introduction of the ammonia at 45 hours on stream, ethylene conversion quickly decreased significantly.

TABLE I

| Example | Conversion | $C_2$-$C_4$ Selectivity | $C_5$-$C_{10}$ Selectivity | $C_{10}^+$ Selectivity |
| --- | --- | --- | --- | --- |
| Example 5 | 92 | 30 | 53 | 17 |
| Example 6 | 38 | 8 | 34 | 58 |
| Example 7 | 75 | 9 | 18 | 73 |
| Example 8 | 74 | 9 | 17 | 74 |
| Example 9 | | | | |
| 5 hours on stream | 77 | 1 | 31 | 68 |
| 20 hours on stream | 7 | 10 | 35 | 55 |
| Example 10 | | | | |
| 10 hours on stream | 90 | 1 | 31 | 68 |
| 35 hours on stream | 65 | 4 | 31 | 65 |
| 45 hours on stream | 63 | 4 | 31 | 65 |
| 70 hours on stream | 30 | 6 | 24 | 70 |

Example 11

The Ammonia Temperature Programmed Desorption (Ammonia TPD) test involves first heating about a 250 milligram sample of catalyst at a rate of about 5° C. per minute to a temperature of about 550° C. in the presence of 20 volume percent oxygen in helium atmosphere at a flow rate of about 100 milliliters per minute. After a hold of about one hour, helium is used to flush the system for about 15 minutes and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium at about 40 milliliters per minute for about 8 hours to remove physisorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is determined by integration.

The ratio of the total amount of ammonia desorbed to the dry weight of the sample yields the Total Acidity. As used herein, values of Total Acidity are given in units of millimoles of ammonia per gram of dry sample. Catalysts active for the oligomerization of dilute ethylene streams are acidic, that is, having a Total Acidity of at least about 0.15, and preferably at least about 0.25, as determined by Ammonia TPD.

The ratio of the total amount of ammonia desorbed from the sample prior to reaching a temperature of 300° C. to the dry weight of the sample yields the Low Temperature Peak. As used herein, values of the Low Temperature Peak are given in units of millimoles of ammonia per gram of dry sample. Catalysts active for the oligomerization of dilute ethylene streams have a Low Temperature Peak, that is having a Low Temperature Peak of at least 0.05, and preferably at least 0.06, as determined by Ammonia TPD.

The ratio of the Low Temperature Peak to the Total Acidity gives a unit-less ratio known as Low Temperature Acidity Ratio. Catalysts resistant to feed impurities in dilute ethylene streams active for the oligomerization of dilute ethylene streams have a Low Temperature Acidity Ratio of at least 0.15, suitably at least 0.2, and preferably greater than 0.25, as determined by Ammonia TPD.

TABLE II

| Catalyst | Total Acidity, millimoles/g | Low Temperature Peak, millimoles/g | Low Temperature Acidity Ratio |
|---|---|---|---|
| Example 1 | 0.323 | 0.116 | 0.36 |
| Example 2 | 0.285 | 0.092 | 0.32 |
| Example 3 | 0.264 | 0.084 | 0.32 |
| Example 4 | 0.311 | 0.037 | 0.12 |

It can be seen from the Examples that the zeolitic catalyst is rendered much less effective in terms of ethylene conversion by feed impurities while the catalysts of the present invention remain an effective ethylene oligomerization catalyst despite the presence of impurities in the feed which are typical catalyst poisons. The catalysts of the present invention maintain ethylene conversions of at least 40 wt-%, typically 60 wt-% and preferably above 70 wt-%.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for oligomerizing ethylene comprising:
providing a feed stream comprising between about 5 and about 50 wt-% ethylene, between about 25 and about 55 wt-% methane and at least one impurity selected from the group consisting of at least about 0.1 wt-% carbon monoxide, at least about 1 wppm hydrogen sulfide, at least about 1 wppm ammonia, at least about 5 wt-% hydrogen and at least about 0.1 wt-% carbon dioxide;
contacting the feed stream with a catalyst comprising an amorphous silica-alumina base with a silica-to-alumina ratio of no more than 20 and a metal selected from the group consisting of Group VIII and Group VIB in the periodic table; and
converting at least 40 wt-% of the ethylene in the feed stream to heavier hydrocarbons.

2. The process of claim 1 wherein said catalyst is an amorphous silica-alumina base impregnated with 0.5-15 wt-% nickel.

3. The process of claim 1 wherein said catalyst has a Low Temperature Acidity Ratio of at least about 0.15 as determined by an Ammonia Temperature Programmed Desorption test.

4. The process of claim 1 wherein said feed stream comprises no more than about 0.5 wt-% propylene.

5. The process of claim 1 wherein said contacting step is performed in a fixed bed of said catalyst.

6. The process of claim 1 wherein said contacting step is performed at a pressure of at least 3,447 kPa.

7. The process of claim 6 wherein said contacting step is performed at a pressure between about 4,826 and about 7,584 kPa.

8. The process of claim 1 wherein said contacting step is performed at a pressure above the critical pressure for ethylene.

9. The process of claim 1 wherein said contacting step is performed at a temperature between about 200° and about 400° C.

10. The process of claim 1 wherein said feed is predominantly in the gas phase.

11. The process of claim 10 wherein said feed stream contacting step is performed at a GHSV 50 to 1000 $hr^{-1}$ on ethylene basis.

12. The process of claim 1 wherein said feed stream comprises between about 10 and about 30 wt-% ethylene.

13. A process for oligomerizing ethylene comprising:
providing a feed stream comprising between about 5 and about 50 wt-% ethylene and between about 25 and about 55 wt-% methane;
contacting the feed stream with a catalyst comprising amorphous silica-alumina base, a silica-to-alumina ratio of no more than 20 and 0.5 to 15 wt-% nickel; and
converting at least 40 wt-% of the ethylene in the feed stream to heavier hydrocarbons.

14. The process of claim 13 wherein said catalyst has a Low Temperature Acidity Ratio of at least about 0.15 as determined by an Ammonia Temperature Programmed Desorption test.

15. The process of claim 13 wherein said contacting step is performed at a pressure between about 4,826 and about 7,584 kPa.

16. The process of claim 13 wherein said contacting step is performed in a fixed bed of said catalyst.

17. The process of claim 13 wherein said contacting step is performed at a pressure of at least 3,447 kPa.

* * * * *